United States Patent
Belvo et al.

(10) Patent No.: US 6,951,840 B2
(45) Date of Patent: Oct. 4, 2005

(54) LIPOGLYCOPEPTIDE ANTIBIOTICS

(75) Inventors: Matthew David Belvo, Greenfield, IN (US); Adam Joseph Kreuzman, Greenwood, IN (US); Palaniappan Kulanthaivel, Carmel, IN (US); Sheng-Bin Peng, Carmel, IN (US); Tim Allen Smitka, Indianapolis, IN (US)

(73) Assignee: Eli Lilly and Company, Indianapolis, IN (US)

( * ) Notice: Subject to any disclaimer, the term of this patent is extended or adjusted under 35 U.S.C. 154(b) by 393 days.

(21) Appl. No.: 10/219,218

(22) Filed: Aug. 14, 2002

(65) Prior Publication Data

US 2003/0130172 A1 Jul. 10, 2003

Related U.S. Application Data

(60) Provisional application No. 60/316,616, filed on Aug. 31, 2001.

(51) Int. Cl.[7] .......................... A61K 38/14; A16K 38/16
(52) U.S. Cl. ............................ 514/8; 530/317; 530/322
(58) Field of Search .............................. 514/8; 530/322, 530/317

(56) References Cited

PUBLICATIONS

Schmid, D.G. et al. P368 Biaryl–bridged lipopeptides from a *Streptomyces* sp. TU 6075, 2nd International Symposium/17th American Peptide Symposium, San Diego, Jun. 9–14, 2001.

*Primary Examiner*—Herbert J. Lilling
(74) *Attorney, Agent, or Firm*—Fay, Sharpe, Fagan, Minnich & McKee, LLP

(57) ABSTRACT

Provided are novel lipoglycopeptides exhibiting bacterial signal peptidase inhibitory activity. Also provided are actinomycete strains that produce these lipoglycopeptides, methods of producing such lipoglycopeptides by culturing these strains, pharmaceutical compositions comprising these lipoglycopeptides, and methods of treating bacterial infections comprising contacting bacteria susceptible to treatment with the present bacterial signal peptidase inhibitor lipoglycopeptides. These lipoglycopeptides are useful in human and veterinary medicine.

3 Claims, 4 Drawing Sheets

LIPOGLYCOPEPTIDE ANTIBIOTICS

This application claims the benefit of Provisional Application No. 60/316,616, filed Aug. 31, 2001.

BACKGROUND OF THE INVENTION

1. Field of the Invention

The present invention relates to the field of pharmaceutical chemistry. More particularly, the present invention relates to the discovery of a group of cyclic lipoglycopeptide inhibitors of bacterial signal peptidase useful as antibiotics. The present invention also relates to the production, isolation, and determination of the structure of a family of new lipoglycopeptides from a member of the family Actinomycetes, i.e., Streptomyces sp., and their biological properties related to bacterial signal peptidase inhibition. In addition, the present invention relates to the novel peptide core of these lipoglycopeptides, and a novel process for deacylating the lipoglycopeptides to generate the peptide core, which can be used in the production of further derivatives. These lipoglycopeptide compounds and derivatives of these compounds can be formulated as pharmaceutical compositions that can be used in the treatment of bacterial infections in mammals. Additionally, these compounds can be formulated as compositions that can be used for controlling the growth of disease-causing bacteria on surfaces requiring disinfection.

2. Description of Related Art

Bacterial Infections and Antibiotic Resistance

Bacterial infections remain the leading cause of death worldwide. *Streptococcus pneumoniae, Staphylococcus aureus, Haemophilus influenzae, Enterococcus sp.,*

*Mycoplasma pneumoniae, Escherichia coli,* and *Enterobacter cloacae* are among the major pathogens causing severe infections, which include otitis, sinusitis, pharyngitis, bronchitis, pneumonia, endocarditis, septicemia, and skin and urinary tract infections. These infections are especially problematic among the immune-compromised populations, e.g., AIDS patients.

Signal Peptidases

Most proteins that are translocated across lipid bilayers are synthesized as precursors (preproteins) with an amino-terminal extension known as a signal (or leader) peptide. This signal sequence is involved in guiding the protein into the targeting and translocating pathway by interacting with the membrane and other components of the cellular secretory machinery (Wickner, et al. (1991) *Ann. Rev. Biochem.* 60, 101–124). The final step in protein translocation and secretion is the release of the mature part of the protein from the membrane, which requires the proteolytic removal of the signal peptide. The proteolytic processing occurs during or shortly after the translocation event and is catalyzed in both prokaryotes and eukaryotes by enzymes known as signal peptidases (SPases). Two major bacterial SPases, SPase I and SPase II, having different cleavage specificities, have been identified. SPase I, also called leader peptidase, is responsible for the processing of the majority of secreted proteins (Dalbey, et al. (1997) *Protein Sci.* 6, 1129–1138; Tschantz, et al. (1994) *Methods Enzymol.* 224, 285–301) whereas SPase II, also called prolipoprotein signal peptidase, exclusively processes glyceride-modified lipoproteins (Innis, et al. (1984) *Proc. Natl. Acad. Sci.U.S.A.* 81, 3708–3712).

Bacterial SPase I possesses unique biochemical and physiological properties. It is one of the essential enzymes in the protein secretion pathway. It is widely distributed in both gram positive and gram negative bacteria, as well as *Chlamydia* (Cregg, et al. (1996) *J. Bacteriol.* 178, 5712–5718; Peng, et al. (2001) *J. Bacterol.* 183, 621–627; Zhang, et al. (1997) *Gene* 194, 249–255).

Signal peptidase is also present in eukaryotic cells; however, the structure of the enzyme from eukaryotic cells is different from that of the bacterial enzyme. Eukaryotic signal peptidase consists of multiple polypeptides. Bacterial SPase I, unlike eukaryotic signal peptidase, consists of a single polypeptide chain.

Additionally, bacterial SPase I and eukaryotic signal peptidase may have distinctive catalytic mechanisms. Evidence suggests that eukaryotic signal peptidase lacks an apparent catalytic lysine, while bacterial SPase I appears to function as a unique serine protease with a serine-lysine catalytic dyad (Sung, et al. (1992) *J. Biol. Chem.* 267, 13154–13159; Black, M. T. (1993) *J. Bacteriol.* 175, 4957–4961; Tschantz, et al. (1993) *J. Biol. Chem.* 268, 27349–27354). Therefore, bacterial SPase I is a good target for the development of antibacterial agents.

Although there are several classes of antibiotics available on the market, the existing and emerging bacterial resistance and cross-resistance to many of the current antibiotics is a growing problem. Thus, there is a continuing need to identify new and quality targets, and to develop novel antibiotics having novel mechanisms of action to overcome such drug resistance.

SUMMARY OF THE INVENTION

Accordingly, to meet the need for new and effective antibiotics, the present inventors have discovered novel lipoglycopeptides having antibiotic activity.

Thus, in a first aspect, the present invention provides an isolated compound comprising the structure shown in formula I:

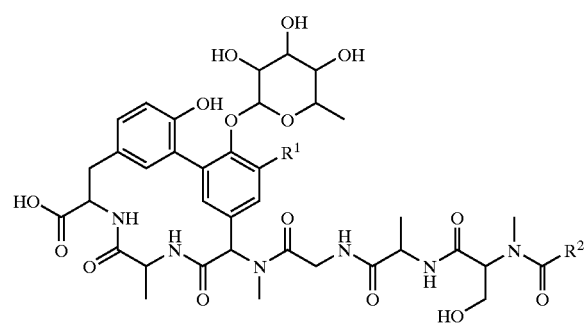

(I)

wherein $R^1$ is H or OH, and $R^2$ is a $C_{14}$–$C_{16}$ alkyl group, or a pharmaceutically acceptable salt thereof.

In another aspect, the present invention provides a compound comprising the structure shown in formula II:

(II)

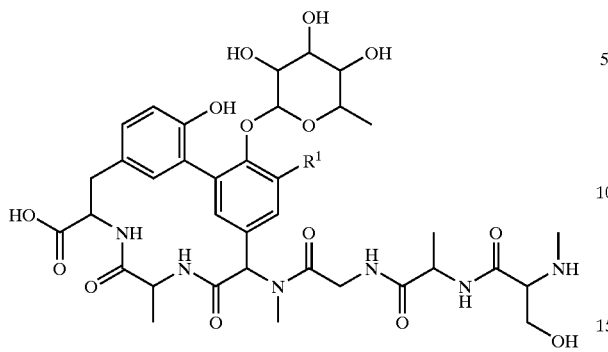

wherein R¹ is H or OH, or a pharmaceutically acceptable salt thereof.

In another aspect, the present invention provides a composition, comprising a compound of formula I, and a buffer, carrier, diluent, or excipient.

In another aspect, the present invention provides a pharmaceutical composition, comprising a compound of formula I, and a pharmaceutically acceptable buffer, carrier, diluent, or excipient.

In another aspect, the present invention provides a pharmaceutical composition, comprising a compound of formula I, an antibacterial compound other than the compound of formula I and/or an antifungal compound, and a pharmaceutically acceptable buffer, carrier, diluent, or excipient.

In another aspect, the present invention provides use of the compound of formula I to prepare a composition or medicament to control the growth of a bacterium susceptible to treatment with said compound. The bacterium can be present on or in a mammal, or on an inert surface.

In a further aspect, the present invention provides a method of controlling the growth of a bacterium susceptible to the antibacterial activity of a compound comprising the structure shown in formula I or a pharmaceutically acceptable salt thereof:

(I)

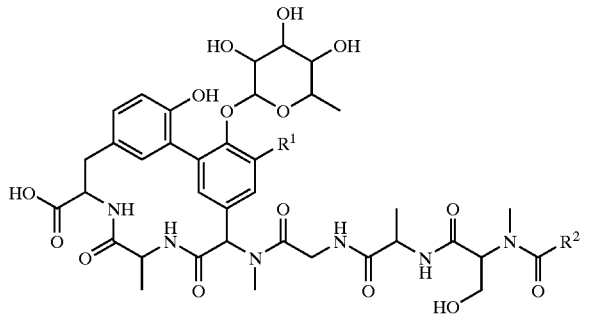

wherein R¹ is H or OH, and R² is a $C_{14}$–$C_{16}$ alkyl group, comprising providing an antibacterial effective amount of the compound of formula I to a locus where the bacterium is present. The locus can be in vivo or in vitro.

In a further aspect, the present invention provides a method of controlling the growth of a bacterium susceptible to the antibacterial activity of a compound comprising the structure shown in formula I or a pharmaceutically acceptable salt thereof:

(I)

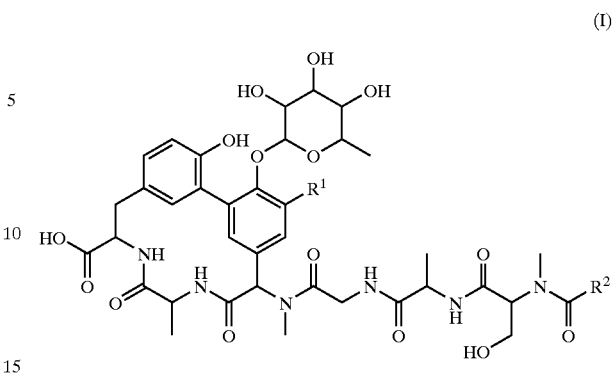

wherein R¹ is H or OH, and R² is a $C_{14}$–$C_{16}$ alkyl group, comprising contacting the bacterium and an antibacterial effective amount of the compound of formula I or a pharmaceutically acceptable salt thereof. The contacting can be performed in vitro or in vivo.

In a further aspect, the present invention provides a method of treating a human or animal subject at risk of contracting, or suffering from, an infection caused by a bacterium susceptible to treatment with the compound of formula I, comprising administering or applying to a human or animal subject an antibacterial effective amount of the compound of formula I.

In yet a further aspect, the present invention provides a biologically pure culture of an actinomycete having all the identifying characteristics of ATCC accession number PTA-3545, ATCC accession number PTA-3546, or ATCC accession number PTA-3547, or a mutant or progeny thereof that produces a compound comprising the structure shown in formula I:

(I)

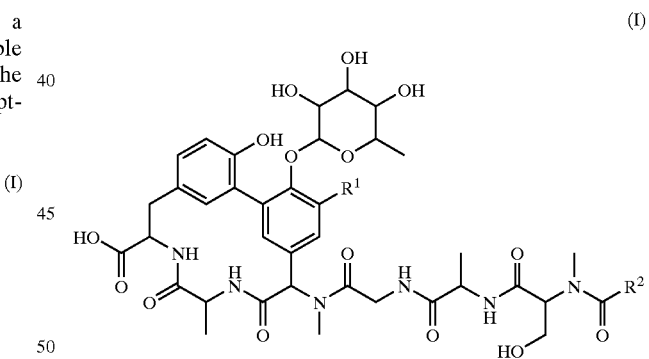

wherein R¹ is H or OH, and R² is a $C_{14}$–$C_{16}$ alkyl group.

In yet a further aspect, the present invention provides a process for producing a bacterial signal peptidase inhibitor, comprising growing a culture of an actinomycete that produces a bacterial signal peptidase inhibitor under conditions and for a time conducive to the production of a bacterial signal peptidase inhibitor and recovering the bacterial signal peptidase inhibitor from the culture. In this process, the actinomycete can have all the identifying characteristics of ATCC accession number PTA-3545, ATCC accession number PTA-3546, or ATCC accession number PTA-3547, or a mutant or progeny thereof that produces a bacterial signal peptidase inhibitor. In addition, in this process, the bacterial signal peptidase inhibitor can comprise the structure shown in formula I:

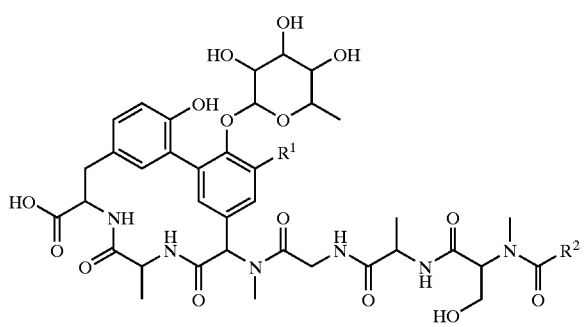

(I)

wherein R¹ is H or OH, and R² is a $C_{14}$–$C_{16}$ alkyl group. Furthermore, this process can be followed by the step of formulating the bacterial signal peptidase inhibitor as a medicament.

In an even further aspect, the present invention provides a process for preparing a compound of formula II, comprising deacylating a lipoglycopeptide comprising the structure shown in formula I:

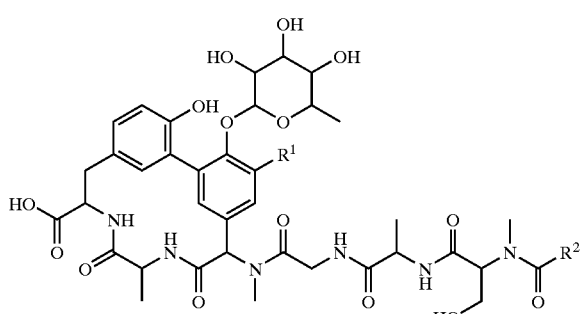

(I)

wherein R¹ is H or OH, and R² is a $C_{14}$–$C_{16}$ alkyl group. The deacylation can be preformed in acetonitrile-water-trifluroacetic acid (6:3:1, v/v/v).

In an even further aspect, the present invention provides a process for preparing a composition or medicament to control the growth of a bacterium susceptible to treatment with a bacterial signal peptidase inhibitor, comprising carrying out the aforementioned processes to produce a compound comprising the structure shown in formula II:

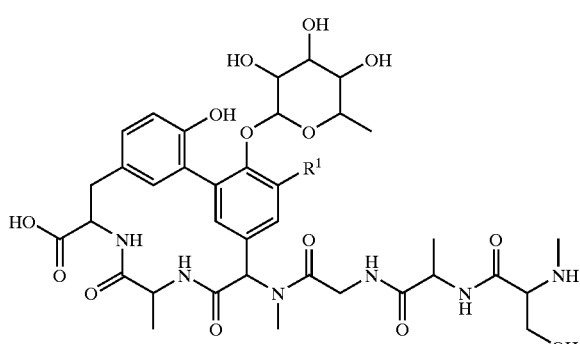

(II)

wherein R¹ is H or OH, followed by reacylating the compound of formula II with an acyl group different from the acyl group in the compound of formula I to produce a compound having antibacterial activity and formulating the compound having antibacterial activity as a composition or medicament.

In an even further aspect, the present invention provides a pharmaceutical pack, comprising a compound comprising the structure shown in formula I or a pharmaceutically acceptable salt thereof:

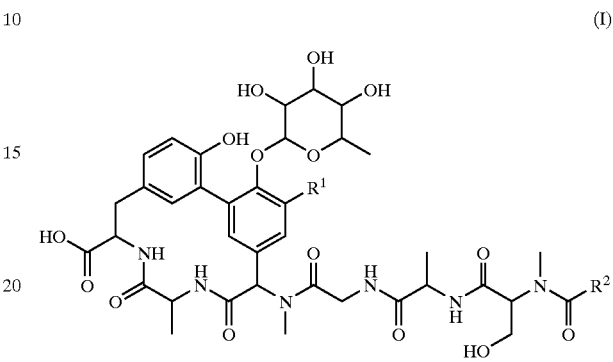

(I)

wherein R¹ is H or OH, and R² is a $C_{14}$–$C_{16}$ alkyl group, a pharmaceutically acceptable buffer, carrier, diluent, or excipient, and instructions for administering or applying the compound to a human or animal subject.

Further scope of the applicability of the present invention will become apparent from the detailed description provided below. However, it should be understood that the detailed description and specific examples, while indicating preferred embodiments of the present invention, are given by way of illustration only since various changes and modifications within the spirit and scope of the invention will become apparent to those skilled in the art from this detailed description.

BRIEF DESCRIPTION OF THE TABLES AND DRAWINGS

The above and other aspects, features, and advantages of the present invention will be better understood from the following detailed description taken in conjunction with the accompanying drawings, all of which are given by way of illustration only, and are not intended in any way to limit the scope of the present invention, wherein.

Figure 1:
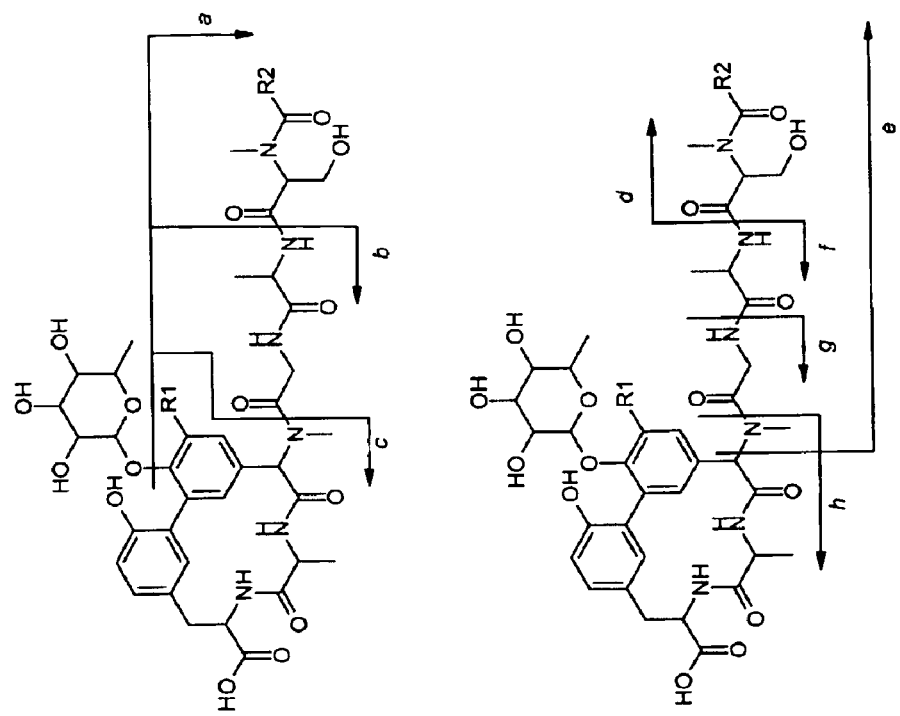
FIG. 1 shows the diagnostic electrospray ionization (ESI) mass spectral fragment patterns of signal peptidase inhibitory lipoglycopeptides 1–8.

Table 1 summarizes $^1$H and $^{13}$C NMR Chemical Assignments of lipoglycopeptide 1 in $CD_3OH$.

Table 2 summarizes the diagnostic EST mass spectral fragments of lipoglycopeptide 1.

Table 3 summarizes ROESY data of lipoglycopeptide 1.

Table 4 summarizes $^1$H and $^{13}$C NMR chemical shift Assignments of lipoglycopeptide 5 in $CD_3OD$.

Table 5 summarizes high resolution ESI mass spectral data of lipoglycopeptides 1–8.

Table 6 summarizes $^1$H and $^{13}$C NMR chemical assignments of glycopeptides 10 and 11 in $CD_3OD$.

Table 7 summarizes inhibition of *E. coli* and *S. pneumoniae* signal peptidases by lipoglycopeptides 1–8.

Table 8 summarizes the inhibitor constants (Ki) of lipoglycopeptides 2, 5, 7, and 8 against *E. coli* signal peptidase 1.

Table 9 summarizes in vitro antibacterial activity of lipoglycopeptides 1, 2, 5, and 6–8.

DETAILED DESCRIPTION OF THE INVENTION

The following detailed description of the invention is provided to aid those skilled in practicing the present invention. Even so, the following detailed description should not be construed to unduly limit the present invention as modifications and variations in the embodiments discussed herein can be made by those of ordinary skill in the art without departing from the spirit or scope of the present inventive discovery.

The contents of each of the references cited herein are herein incorporated by reference in their entirety.

Definitions

The following definitions are provided to aid those of ordinary skill in the art in understanding the disclosure herein. These definitions are intended to correspond to those known in the art, and are therefore not limited to the specific definitions given, but are used according to the state of the art, as demonstrated by cited and/or contemporary publications or patents.

As used herein, the term "alkyl" refers to a hydrocarbon radical containing the stated number of carbon atoms. The alkyl radical may be straight (e.g., methyl, ethyl, propyl, butyl, etc.)or branched (e.g., isopropyl, isobutyl, tertiary butyl, neopentyl, etc.).

As used herein, the term "inert surface" means a nonreactive surface with the potential for bacterial contamination, for example but not limited to, surgical instruments, catheters, countertops, garbage containers, restroom facilities and equipment, and restaurant equipment.

As used herein, the term "isolated" when applied to the lipoglycopeptides of the present invention refers to such lipoglycopeptides when removed from their naturally occurring location, i.e, within actinomycetes cells, and/or lipoglycopeptides that have been purified to remove at least some portion of cellular or non-cellular molecules with which the lipoglycopeptides are naturally associated or in proximity within actinomycetes cells or cultures.

As used herein, the term "mammal" includes humans, companion animals (e.g., dogs, cats and horses), zoo animals (e.g., zebras, elephants, etc.), and food-source animals (e.g., cows, pigs, goats, and sheep).

As used herein, the term "poultry" refers to avians such as chickens, ducks, pheasants, and turkeys.

As used herein, the term "mutant" refers to an organism in which a mutation has occurred. A mutation is a change in the quantity or structure of the genetic material of that organism, which may or may not affect the organism's phenotype. Exemplary types of mutations include, but are not limited to, point mutations and frameshift mutations.

Mutations can be induced following exposure of organisms to chemical, physical, or biological mutagens, i.e., agents capable of causing a change in DNA, resulting in a change in genetically encoded information.

Chemical mutagens include, for example, various alkylating agents (e.g., ethyl methane sulfonate, nitrogen mustards, mitomycin, nitrosoguanidine), base analogs (e.g., 5-bromouracil, 2-aminopurine), intercalating agents (e.g., acridine dyes, ethidium bromide), bisulfite, hydroxylamine, and nitrous acid.

Physical mutagens include, for example, ionizing radiation, ultraviolet light, and heat.

Biological mutagens include, for example, transposable elements.

Mutations in DNA can also be generated in vitro by a variety of different recombinant and non-recombinant DNA techniques, including, for example, enzymatic mutagenesis using DNA polymerase; alteration (creation or removal) of restriction sites or insertion or deletion of DNA sequences using appropriate enzymes including restriction endonucleases, DNA polymerases, exonucleases, ligases, and restriction fragments or chemically synthesized oligonucleotides; insertion or deletion of nucleotides using oligonucleotide-directed mutagenesis (site-directed mutagenesis); cassette mutagenesis; PCR; etc.

The various methods of mutagenesis discussed above, as well as others, are well know to those of ordinary skill in the art. For example, see Sambrook et al. (1989) *Molecular Cloning: A Laboratory Manual*, Second Edition, Cold Spring Harbor Laboratory Press, Cold Spring Harbor, N.Y., and Ausubel et al. (1989) *Current Protocols in Molecular Biology*, John Wiley & Sons, Inc.).

Mutations can also arise spontaneously as a result of events such as errors occurring in DNA replication, or the movement of transposable genetic elements normally present within genomes.

As used herein, the term "progeny" refers to offspring of a parent organism.

The term "susceptible bacteria" refers to bacteria that possess signal peptidases that are inhibited by the present lipoglycopeptides. Non-limiting examples of susceptible bacteria include *Staphylococcus aureus, Streptococcus pneumoniae, Streptococcus pyogenes, Enterococcus faecalis, Enterococcus faecium, Mycoplasma pneumoniae, Haemophilus influenzae, Escherichia coli, Neisseria meningitidis*, and *Chlamydia pneumoniae*.

As used herein, the term "susceptible to treatment with said compound" refers to a bacterium or bacterial infection that responds to treatment with a lipoglycopeptide of the present invention. Such response can include a bacteriostatic effect or a bactericidal effect. Alternatively, susceptibility to treatment can also refer to a situation wherein the pathogenic effect(s) of susceptible bacteria are ameliorated or alleviated, even in the absence of an effect on bacterial cell growth or viability.

Bacterial SPase as an Antimicrobial Target

Bacterial SPase I is an attractive target for the development of anti-bacterial agents. In particular, the location of bacterial SPase I within the bacterial cell, as opposed to the location of signal peptidase in the eukaryotic cell, makes bacterial SPase I a particularly attractive target. The active domain of bacterial SPase I is exposed to the surface of the bacterial cytoplasmic membrane and is thus readily accessible to potential inhibitors. However, the active domain and most other parts of the eukaryotic enzyme complex are located in the lumenal side of the microsomes. Thus, any potential inhibitor would have to cross the cytoplasmic and the microsomal membranes to have access to the active site. This, coupled with its other unique biological and biochemical features such as catalytic mechanism, make bacterial SPase I a new and highly desirable target for the development of antibiotics and surface disinfectants.

Lipoglycopeptides that Inhibit SPase I

The present inventors have isolated three actinomycete strains, each of which produces novel compounds having the following structural formula:

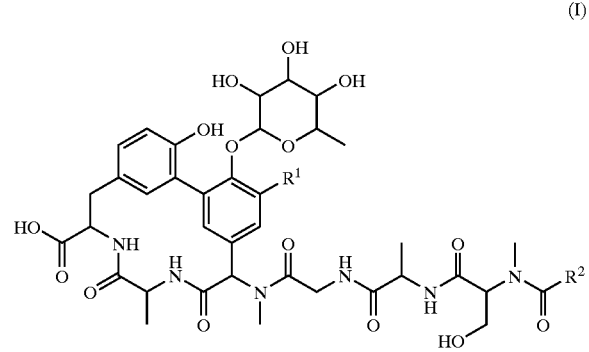

(I)

wherein:
R$^1$ is OH or H; and
R$^2$ is a C$_{14}$–C$_{16}$ alkyl group.

The present actinomycete strains have been deposited with the American Type Culture Collection, 10801 University Boulevard, Manassas, Va. 20110-2209 under accession numbers ATCC No. PTA-3545, ATCC No. PTA-3546, and ATCC No. PTA-3547 under the terms of the Budapest Treaty on Aug. 13, 2001.

In vitro testing, for example fluorimetric assaying of these compounds (Peng, et al. (2001) Anal. Biochem. 293, 88–95), reveals that each of the eight lipoglycopeptides discussed herein exhibits bacterial SPase I inhibitory activity and hence inhibits bacterial growth, making these compounds suitable candidates for development as antimicrobial agents.

Although a family of lipopeptides, called arylomycins, has recently been disclosed (Schmid, D. G. et al. P368 Biaryl-bridged lipopeptides from a *Streptomyces sp.* TU 6075, 2$^{nd}$ International Symposium/17$^{th}$ American Peptide Symposium, San Diego, Jun. 9–14, 2001), the arylomycins lack the deoxy-α-mannose unit, and have not been shown to be SPase I inhibitors. Several of these compounds exhibited antimicrobial activity against gram positive bacteria by zone inhibition assay.

In general, the compounds of the present invention can be prepared, for example, by starting with an actinomycete culture, using it to inoculate a vegetative culture medium, incubating the culture medium to produce a vegetative culture, and streaking an aliquot on a TSB (BBL Cat. # 211771) (Trypticase Soy Broth) agar plate to verify that the culture is axenic. The axenic vegetative culture is then used to inoculate fermentation flasks, the inoculated flasks are incubated, and the fermentation broth is harvested. The whole broth is then centrifuged. The cell mass is separated from the supernatant, extracted, and the extract is concentrated, and partitioned with alcoholic and ethyl acetate solvents. The ethyl acetate upper layer is removed and the remaining solution further partitioned by adding additional ethyl acetate. The two ethyl acetate upper layers are combined and evaporated in vacuo to a residue. The residue is suspended in a mixture of alcohol-water and the insoluble materials removed by filtration. The filtrate is then diluted and the solution applied to chromatographic columns for separation of the lipoglycopeptides.

Therapeutic Applications

As used herein, the term "therapeutically effective amount" or "antibacterial effective amount" means an amount of compound of the present invention, or combination of compounds as disclosed herein, which is effective in reducing, ameliorating, or alleviating conditions or symptoms associated with a bacterial infection or associated pathogenesis in patients, or in reducing bacterial levels in vitro or in vivo of bacteria susceptible to the inhibitory activity of these compounds. Susceptible bacteria are those that possess signal peptidases that are inhibited by the present lipoglycopeptides.

The specific dose of a compound administered according to the present invention will, of course, be determined by the particular circumstances surrounding the case including, for example, the compound administered, the route of administration, the state of being of the patient, and the pathological condition being treated. A typical daily dose for human use will contain a nontoxic dosage level of from about 1 mg to about 1000 mg/day of a compound of the present invention. Preferred daily doses generally will be from about mg to about 750 mg/day. More preferred are 10 mg, 20 mg, 30 mg, 40 mg, 50 mg, 60 mg, 70 mg, 80 mg, 90 mg, and 100 mg, administered once to three times per day. Other therapeutically or antibacterial effective amounts of a compound of the present invention can be determined using techniques that are well-known to the skilled artisan. Note, for example, Benet et al., in *Goodman & Gilman's The Pharmacological Basis of Therapeutics*, Ninth Edition, Hardman et al., Eds., McGraw-Hill, New York (1996), Chapter 1, pp. 3–27, and the references cited therein. Thus, the appropriate formulations, dose(s) range, and dosing regimens of such a compound can be easily determined by routine methods.

It should be noted that lipoglycopeptides of the present invention can be formulated as pharmaceutically acceptable salts or prodrugs. The salts of the above lipoglycopeptide compounds represented by formula I are an additional aspect of the invention. In those instances where the compounds of the invention possess acidic or basic functional groups, various salts may be formed which are more water soluble and physiologically suitable than the parent compound. Representative pharmaceutically acceptable salts include, but are not limited to, the alkali and alkaline earth salts such as lithium, sodium, potassium, calcium, magnesium, aluminum and the like. Salts are conveniently prepared from the free acid by treating the acid in solution with a base or by exposing the acid to an ion exchange resin. Included within the definition of pharmaceutically acceptable salts are the relatively non-toxic, inorganic and organic base addition salts of compounds of the present invention, for example, ammonium, quaternary ammonium, and amine cations, derived from nitrogenous bases of sufficient basicity to form salts with the compounds of this invention (see, for example, Berge, et al., (1977) *J. Phar. Sci.*, 66: 1–19).

Certain compounds of the invention may possess one or more chiral centers and may thus exist in optically active forms. Additional asymmetric carbon atoms can be present in a substituent group such as an alkyl group. All such isomers as well as the mixtures thereof are intended to be included in the invention. If a particular stereoisomer is desired, it can be prepared by methods well known in the art by using stereospecific reactions with starting materials which contain the asymmetric centers and are already resolved or, alternatively by methods which lead to mixtures of the stereoisomers and subsequent by known methods. For example, a racemic mixture may be resolved by treating with a single enantiomer of some other compound. This changes the racemic form into a mixture of diastereomers, and diastereomers because they have different melting points, different boiling points, and different solubilities can be separated by conventional means, such as crystallization.

Prodrugs are derivatives of the compounds of the invention which have chemically or metabolically cleavable groups and become by solvolysis or under physiological conditions the compounds of the invention which are pharmaceutically active in vivo. Derivatives of the compounds of this invention have activity in both their acid and base derivative forms, but the acid derivative form often offers advantages of solubility, tissue compatibility, or delayed release in a mammalian organism (see, Bundgard, H., (1985) *Design of Prodrugs*, pp. 7–9, 21–24, Elsevier, Amsterdam). Prodrugs include acid derivatives well known to practitioners of the art, such as, for example, esters prepared by reaction of the parent acidic compound with a suitable alcohol, or amides prepared by reaction of the parent acid compound with a suitable amine. Simple aliphatic or aromatic esters derived from acidic groups pendent on the compounds of this invention are preferred prodrugs. In some cases it is desirable to prepare double ester type prodrugs such as (acyloxy) alkyl esters or ((alkoxycarbonyl)oxy)alkyl esters. Particularly preferred esters as prodrugs are methyl, ethyl, propyl, isopropyl, n-butyl, isobutyl, tert-butyl, morpholinoethyl, and N,N-diethylglycolamido. N,N-diethylglycolamido ester prodrugs may be prepared by reaction of the sodium salt of a compound of formula I (in a medium such as dimethylformamide) with 2-chloro-N,N-diethylacetamide (available from Aldrich Chemical Co., Milwaukee, Wis. USA; Item No. 25,099-6). Morpholinylethyl ester prodrugs may be prepared by reaction of the sodium salt of a compound of formula I (in a medium such as dimethylformamide) 4-(2-chloroethyl)morpholine hydrochloride (available from Aldrich Chemical Co., Milwaukee, Wis. USA, Item No. C4, 220-3).

It should also be noted that the present lipoglycopeptides can be used individually or in combination with one another. In addition, these compounds can also be used in combination with conventional antibiotics and antifungal compounds. The individual drugs or drug combinations of the present invention can be provided to a cell or cells, to an inert surface, or to a human patient, either in separate pharmaceutically acceptable formulations administered simultaneously or sequentially, formulations containing more than one therapeutic agent, or by an assortment of single agent and multiple agent formulations. However administered, these drug combinations form an effective amount of components.

Doses of compounds can be administered to a patient in a single dose or in proportionate multiple subdoses. In the latter case, dosage unit compositions can contain such amounts of submultiples thereof to make up the daily dose. Multiple doses per day can also increase the total daily dose should this be desired by the person prescribing the drug.

The regimen for treating a patient suffering from a bacterial infection with the compounds and/or compositions of the present invention is selected in accordance with a variety of factors, including the age, weight, sex, diet, and medical condition of the patient, the severity of the infection, the route of administration, pharmacological considerations such as the activity, efficacy, pharmacokinetic, and toxicology profiles of the particular compounds employed, and whether a drug delivery system is utilized. Administration of the single or multiple drug combinations disclosed herein should generally be continued over a period of several weeks to several months or years until the infection has been controlled or eradicated. Patients undergoing treatment with the drugs disclosed herein can be routinely monitored by, for example, measuring bacterial counts; monitoring patient temperature; monitoring the presence of bacterial antigens; tissue or organ inflammation; diminution of pain, redness, tenderness, and swelling; reduction in malaise; diminution in pathological symptoms; etc. Continuous analysis of the data obtained by these methods permits modification of the treatment regimen during therapy so that optimal amounts of each drug component are administered, and so that the duration of treatment can be determined as well. Thus, the treatment regimen/dosing schedule can be rationally modified over the course of therapy so that the lowest amounts of each of the antibacterial compounds used which exhibit satisfactory effectiveness are administered, and so that administration of such antibacterial compounds is continued only so long as is necessary to successfully treat the infection.

Compounds of the present invention can be used in combination with other antibiotics, for example but not limited to, Penicillins (Penicillin, Ampicillin, Amoxicillin, Oxacillin, Methicillin, Ticarcillin, etc.); Cephalosporins (Cephalothin, Cafazolin, Cephapirin, Cefaclor, Cefamandole, Cefuroxime, Cefotaxine Cefoperazone, etc.); other beta-lactam drugs (Aztreonam, imipenem-cilastatin, etc.); Aminoglycosides (Gentamicin, Tobramycin, Amikacin, Netimicin, etc.); Quinolones (Nalidixic acid, Cinoxacin, Norfloxacin, Ciprofloxacin, etc.); Other antibiotics (Chloramphenicol, Erythromycin, Metronidazole, Rifampin, Sulfonamides, Trimethoprin, Tetracycline, Vancomycin, Spectinomycin, etc.) and/or in conjunction with an antifungal, for example but not limited to, Polyenes (Amphotericin B, Nystatin); 5-Fluorocytosine; Azoles (Miconazole, Ketoconazole, etc.); Allylamines (Naftifine, Terbinafine, etc.); Lipopeptides (Cilofungin, etc.) to treat a bacterial and/or fungal infection.

Additionally, the compounds of the present invention can be used alone or in combination with the aforementioned antibiotics, and/or in conjunction with recombinant activated protein C in treating systemic bacterial infections.

Compounds can be administered by a variety of routes including enteral, parenteral, and topically, for example, orally, aerosol, rectally, transdermally, subcutaneously, intravenously, intramuscularly, and intranasally.

These compounds preferably are formulated prior to administration, the selection of which will be decided by the attending physician. Thus, another aspect of the present invention is a pharmaceutical composition comprising an effective amount of a compound of formula I, or a pharmaceutically acceptable salt thereof, and a pharmaceutically acceptable carrier, diluent, or excipient. The total active ingredients in such formulations comprises from 0.1% to 99.9% by weight of the formulation. By "pharmaceutically acceptable" it is meant the carrier, diluent, excipients and salt must be compatible with the other ingredients of the formulation, and not deleterious to the recipient thereof.

Pharmaceutical formulations of the present invention can be prepared by procedures known in the art using well known and readily available ingredients. For example, the compounds of formula I can be fonmulated with common excipients, diluents, or carriers, and formed into tablets capsules, suspensions, powders, and the like. Examples of excipients, diluents, and carriers that are suitable for such fonmulations include the following: fillers and extenders such as starch, sugars, mannitol, and silicic derivatives; binding agents such as carboxymethyl cellulose and other cellulose derivatives, alginates, gelatin, and polyvinylpyrrolidone; moisturizing agents such as glycerol; disintegrating agents such as calcium carbonate and sodium bicarbonate; agents for retarding dissolution such as paraffin; resorption accelerators such as quaternary ammonium compounds; surface active agents such as cetyl alcohol, glycerol monostearate; adsorptive carriers such as kaolin and bentonite; and lubricants such as talc, calcium and magnesium stearate, and solid polyethyl glycols.

The compounds also can be formulated as elixirs or solutions for convenient oral administration or as solutions appropriate for parenteral administration, for example, by intramuscular, subcutaneous or intravenous routes.

Additionally, the compounds are well suited to formulation as sustained release dosage forms and the like. The formulations can be so constituted that they release the active ingredient only or preferably in a particular physiological location, possibly over a period of time. The coatings, envelopes, and protective matrices may be made, for example, from polymeric substances or waxes.

Further, the compositions disclosed herein can be used to control the growth of bacteria susceptible to the antimicrobial activity of the lipoglycopeptides discussed herein when present on inert surfaces. By "control the growth" is meant retarding or inhibiting the growth of, stopping the growth of, or killing, the bacteria. This results in a reduction in the adverse effects caused by the presence of the bacteria in any particular locus or milieu. These compositions can be formulation by conventional methods, and can contain formulation aids such as carriers, diluents, inert materials, surfactants, solvents, and other additives well known in the art. Pharmaceutically acceptable carriers are disclosed, for example, in the Pharmacopeia of the United States and the National Formulary. Using these formulations, mixtures of the present lipoglycopeptides with other antimicrobial substances, such as conventional antibiotics and antifungals can also be prepared.

The compounds can be applied directly to loci where undesirable bacteria are present, alone or in a mixture with active ingredients, carriers, diluents, or other additives, including other antimicrobial agents, as is known in the art.

The following examples are provided to illustrate various aspects of the present invention, and should not be construed to be limiting thereof in any way.

All solvents used herein are reagent grade. The solvents and other reagents mentioned below can be obtained from commercial suppliers such as Fisher Scientific, Sigma-Aldrich, etc., as is well known in the art.

EXAMPLE 1

Preparation of Inocula

Aliquots of actinomycete culture ATCC No. PTA-3545, ATCC No. PTA-3546, and ATCC No. PTA-3547, stored in the vapor phase of liquid nitrogen, are thawed and used to inoculate 20 ml portions of vegetative medium. The vegetative medium is composed of (in g/l) tryptic soy broth (BBL Cat. # 211771) (30), yeast extract (DIFCO Cat. # 212730) (3), $MgSO_4 \cdot 7H_2O$ (2), glucose (5), and maltose (4). Approximately 100 μls of thawed cells are used to inoculate a ml portion of the vegetative medium contained in 100 ml plastic bottles fitted with a vented membrane cap (Performance Systematix, Inc., Caledonia, Mich., cat # MRP28-400). The bottles are then incubated with shaking at 165 rpm at 30° C., for 72 hr. At the end of the incubation period, an aliquot of each vegetative culture is streaked on TSB (Trypticase Soy Broth) agar plates to ensure that the culture is axenic.

EXAMPLE 2

Production of Novel Lipoglycopeptides 1–8

2 ml of axenic vegetative culture as described in Example 1 are inoculated into 800 ml of fermentation medium contained in 2.5 liter non-baffled plastic conical flasks (Scandia Plastics, Sheboygan, Wis.) covered with two layers of Bio-Shield paper (Baxter Healthcare Corp., Deerfield, Ill., cat. # 4008). The fermentation medium is composed of (per liter): MOPS (3-[N-morpholino]propane-sulfonic acid)-Na salt, pH 7.0 (23.1 g), $CaCO_3$ (g), $CaCl_2 \cdot 2H_2O$ (0.228 g), $MgSO_4 \cdot 7H_2O$ (1 g), 1000× trace metal mix (1 ml), 100× vitamin mix (10 ml), glucose (9 g), potato starch (0.5 g), $(NH_4)_2SO_4$ (0.1 g), and Pharmamedia (Traders Protein, Division of Archer Daniels Midland Company, Memphis, Tenn.) (9 g). The 100× trace metal mix is composed of (g/l): Fe-EDTA (3.5), $CuSO_4 \cdot 5H_2O$ (0.5), $Na_2MoO_4 \cdot 2H_2O$ (0.5), $FeSO_4 \cdot 7H_2O$ (0.5), $ZnSO_4 \cdot 7H_2O$ (0.4), $MnCl_2 \cdot 4H_2O$ (0.02), $CoCl_2 \cdot 6H_2O$ (0.01), $NiCl_2 \cdot 6H_2O$ (0.01), and $H_3BO_3$ (0.015). The 1000× vitamin stock is composed of (g/l): biotin (0.02), folate (0.02), thiamine-HCl (0.05), calcium pantothenate (0.05), vitamin B12 (0.001), riboflavin (0.05), and nicotinamide (0.05). The vitamin stock is diluted 1:10 with deionized water before addition to the fermentation medium. Inoculated flasks are incubated at 30° C. while shaking at 250 rpm. After 96 hours, the shaking is stopped and the fermentation broth is harvested.

EXAMPLE 3

Isolation of Lipoglycopeptides 1–8

The whole broth (40 flasks×800 ml) of Example 2 is centrifuged using a Beckman J6B centrifuge JS-5.2 rotor at 2100 rpm for 15 min. The supernatant is removed from the cell pellet and is discarded. The pellet is extracted twice, each time with liters of methanol. The combined methanol extracts (liters) are concentrated in a rotary evaporator to approximately 500 ml (mostly aqueous) and partitioned with 500 ml of reagent grade methanol and 1 liter of reagent grade ethyl acetate. The ethyl acetate upper layer is removed and the remaining solution is further partitioned with 1 liter of reagent grade ethyl acetate. The two ethyl acetate upper layers are combined and evaporated in vacuo to a residue (49 g). The residue is suspended in 300 ml of 3:1 (v/v) methanol-water, and the insoluble materials are removed using a 0.2 micron membrane filter (Corning® Cat. # 430773). The clear filtrate is then diluted with approximately 600 ml of deionized water to adjust the methanol-water ratio to 1:3 (v/v). This solution is applied to a TosoHaas Amberchrom CG161m (Cat. # 430773) column (100 ml) equilibrated with 3:1 (v/v) water-methanol and sequentially eluted with 4 column volumes of 3:1 (v/v) water-methanol, 4 column volumes of 1:1 (v/v) water-methanol, and 2×4 column volumes of methanol. The first 4-column volumes of methanol effluent are concentrated in vacuo to yield approximately 2 g of a solid residue. The solid residue is dissolved in methanol and chromatographed over a Sephadex LH-20 (Pharmacia, Cat. # 17-0090-02) column (7.5×39 cm) with reagent grade methanol as the solvent. The first 600 ml of effluent are discarded; the next 600 ml of effluent are collected and evaporated to yield 960 mg of a solid. This solid is dissolved in ml of reagent grade methanol and further chromatographed over a Waters SymmetryPrep™ $C_{18}$ column (Cat. # WAT248000) (50×250 mm, 7 micron, flow rate 45 ml/min., 35–70% acetonitrile gradient buffered with 0.05% ammonium acetate over 48 min and holding at 70% acetonitrile for 24 min). Fractions are collected at an interval of 1 min. A total of 72 fractions are collected and are appropriately combined to yield three major fractions A (172 mg), B (370 mg), and C (128 mg).

Fraction C (128 mg) is further chromatographed over a PolyLC polyhydroxyethyl aspartamide™ column (PolyLc Inc. Cat. # BMHY 1201) (25.4×250 mm, 12 micron, flow rate ml/min., 95–70% acetonitrile gradient buffered with 0.05% ammonium acetate over 50 min. and holding at 70% for 22 min). 72×1 minute fractions are collected and combined to yield two fractions, D (40 mg) mostly containing lipoglycopeptides 1 and 2 and fraction E (12.5 mg) containing lipoglycopeptides 3, 4, and 5.

0.3 mg of lipoglycopeptice 3, 0.5 mg of lipoglycopeptide 4 and 3.2 mg of lipoglycopeptide 5.

Fraction A (172 mg) is chromatographed over a PolyLC polyhydroxyethyl aspartamide™ column (PolyLc Inc. Cat. # BMHY1201) (25.4×250 mm, 12 micron, flow rate 45 ml/min, 95–65% reagent grade acetonitrile gradient over 48 min. and holding at 65% reagent grade for 24 min.) to

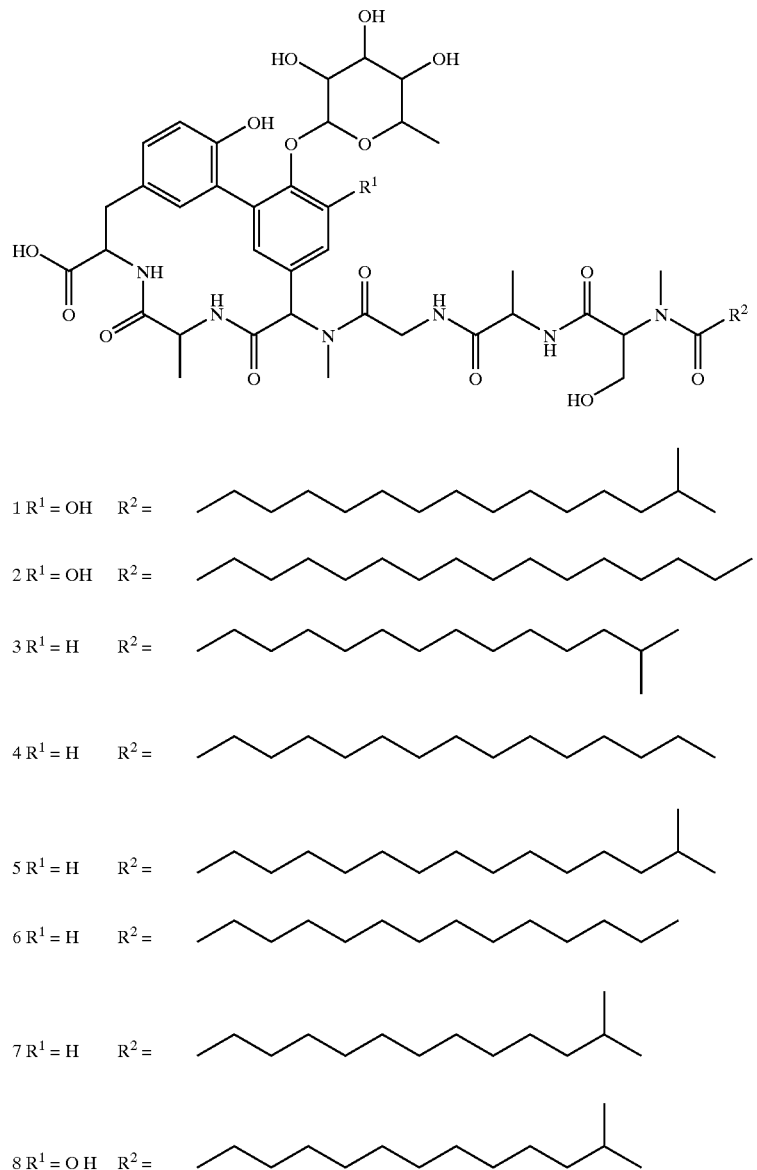

Rechromatography of fraction D over a Waters SymmetryPrep™ $C_{18}$ column (Cat. # WAT066235) (7.8×300 mm, 7 micron, flow rate 4.7 ml/min., 40–55% acetonitrile gradient buffered with 0.05% ammonium acetate over 60 min.) affords 11.7 mg of lipoglycopeptide 1 and 4.1 mg of lipoglycopeptide 2. Repeat chromatography of fraction E twice on a Waters SymmetryPrep™ $C_{18}$ column) (Cat. # WAT066235) (7.8×300 mm, 7 micron, flow rate 4.7 ml/min., 40–55% reagent grade acetonitrile gradient buffered with 0.05% reagent grade ammonium acetate over 60 min.) yields furnish fractions F (90 mg) containing lipoglycopeptides 6 and 7 and G (51 mg) containing lipoglycopeptide 8.

Rechromatography of fraction F over a Waters SymmetryPrep™ $C_{18}$ column (Cat. # WAT066245) (19×300 mm, 7 micron, flow rate 17 ml/min., 25–40% reagent grade acetonitrile gradient buffered with 0.05% reagent grade ammonium acetate over 48 min. and holding at 40% reagent grade acetonitrile for 24 min.) affords 9 mg of enriched 6 and 11 mg of enriched lipoglycopeptide 7. Each sample is re-purified as detailed above to yield 3.7 mg of lipoglycopeptide 6 and 2.3 mg of lipoglycopeptide 7. Similar chromatography of fraction G (51 mg) over a Waters Symmetry Prep™ $C_{18}$ column (Cat. # WAT066245) as detailed for fraction F gives 6.4 mg of lipoglycopeptide 8.

EXAMPLE 4

Structure Determination

MS Studies

LC-MS of all compounds is carried out using a Waters Alliance 2690 Separations Module. High resolution mass determinations (HRESIMS) are obtained using a Micromass Q-TOF 1 quadrupole/orthogonal time-of-flight mass spectrometer. All accurate mass determinations use the desvancosamine ion (m/z 1305.3434) of vancomycin as the lock mass.

NMR Studies

NMR experiments are carried out on a Varian Inova spectrometer equipped with a pulse-field gradient and a Nalorac Z-SPEC® microdual 3 mm probe, operating at 500 MHz for $^1$H and 125.7 MHz for $^{13}$C. All proton and carbon chemical shifts are referred to the solvent signal ($CD_3OH$ or $CD_3OD$) at 3.30 ppm and 49 ppm, respectively. The two-dimensional total correlation spectroscopy (TOCSY), double-quantum filtered correlation spectroscopy (DQCOSY), heteronuclear single-quantum correlation (HSQC), heteronuclear multiple-bond correlation (HMBC) and rotating frame nuclear Overhauser effect Spectroscopy (ROESY) are performed using Varian standard pulse sequences.

Amino Acid Analysis

Approximately 100 μg of the peptide is reconstituted with 300 μl of 0.01 N hydrochloric acid. To 100 μl of this solution 6 N hydrochloric acid containing 1% phenol (v/v) is added and the mixture is heated at 110° C. for 24 hr. Then the mixture is evaporated to dryness, reconstituted with 150 μl of 0.01 N hydrochloric acid and an aliquot (25 μl) is used for amino acid analysis. The amino acids are pre-column derivatized with phenylisothiocyanate and separated on a Brownlee™ PTC-18 column (Perkin Elmer Cat. # 0711-0204) Mobile phase A: Water buffered with 50 mM sodium acetate pH 5.2. Mobile phase B: 70% acetonitrile containing 30% 32 mM sodium acetate in water. The column is eluted with a step gradient starting from 4% B to 100% of B in 20 min.).

The new isomeric lipoglycopeptides 1 and 2 show identical molecular composition ($C_{52}H_{78}N_6O_{16}$) as determined by high resolution ESIMS (Electrospray Ionization Mass Spectrometry)(Calculated for $C_{52}H_{79}N_6O_{16}$ 1043.5553 (M+H), observed 1043.5531 and 1043.5551, respectively. The structures of lipoglycopeptides 1 and 2 are primarily determined by NMR spectroscopy. After trial and error experiments, the optimum resolution of the amide proton signals in the $^1$H spectrum of lipoglycopeptide 1 is observed at 10° C. in $CD_3OH$ solution. This condition is employed to perform both one- and two-dimensional NMR experiments. Detailed analysis of $^1$H, $^{13}$C, DQCOSY, TOCSY, HSQC, and HMBC data enables the assignment of all proton and carbon resonances of lipoglycopeptide 1 (Table 1), and reveals the presence of four common amino acid residues, i.e., glycine, two alanines, and N-methylserine, in addition to two uncommon aromatic amino acid residues, i.e., a 3-substituted tyrosine and a 3,4,5-trisubstituted N-methylphenylglycine.

TABLE 1

$^1$H and $^{13}$C NMR Chemical Assignments of lipoglycopeptide 1 in CD3OH

| AA | Position | $^1$H δ | M (J Hz) | $^{13}$C δ | m |
|---|---|---|---|---|---|
| NMeSer | N—CH$_3$ | 3.09 | s | 33.7 | q |
| | CO | — | | 171.8 | s |
| | α | 4.97 | dd (8, 6) | 60.9 | d |
| | β1 | 4.02 | dd (11.5, 6) | 60.6 | t |
| | β2 | 3.91 | dd (11.5, 8) | | |
| Ala 1 | NH | 8.33 | d (7.5) | — | |
| | CO | | | 175.2 | s |
| | α | 4.47 | quint (7.5) | 50.4 | d |
| | β | 1.38 | d (7.5) | 18.0 | q |
| Gly | NH | 8.30 | t (5.5) | — | |
| | CO | | | 171.5 | s |
| | α1 | 4.22 | dd (17, 5.5) | 42.4 | t |
| | α2 | 4.07 | dd (17, 5.5) | | |
| PheGly | N—CH$_3$ | 2.82 | s | 32.6 | |
| | CO | | | 171.8 | s |
| | α | 6.25 | brs | 61.8 | d |
| | 1 | — | | 132.4 | s |
| | 2 | 6.77 | brs | 117.0 | d |
| | 3 | — | | 151.6 | s |
| | 4 | — | | 143.8 | s |
| | 5 | — | | 135.7 | s |
| | 6 | 6.47 | d (1.5) | 126.8 | d |
| Ala 2 | NH | 8.54 | d (8.5) | — | |
| | CO | | | 173.4 | s |
| | α | 4.79 | quint (7.5) | 50.6 | d |
| | β | 1.31 | d (7) | 19.2 | q |
| Tyr | NH | 8.35 | d (8) | — | |
| | CO | | | 178.4 | s |
| | α | 4.56 | m | 56.2 | d |
| | β1 | 3.38 | dd (16.5, 3) | 35.5 | t |
| | β2 | 3.07 | dd (16, 9) | | |
| | 1 | — | | 130.1 | s |
| | 2 | 6.86 | d (1.5) | 134.0 | d |
| | 3 | — | | 127.5 | s |
| | 4 | — | | 153.3 | s |
| | 5 | 6.78 | d (8) | 117.3 | d |
| | 6 | 7.03 | dd (8, 1.5) | 130.7 | d |
| Sugar | 1' | 5.36 obsc. | | 103.9 | d |
| | 2' | 4.26 | brm | 72.1 | d |
| | 3' | 3.75 | dd (9.5, 3) | 72.3 | d |
| | 4' | 3.26 | t (9.5) | 73.2 | d |
| | 5' | 3.19 | dq (9.5, 6.5) | 71.4 | d |
| | 6' | 0.64 | d | 17.4 | q |
| Side chain | 1" | — | | 176.9 | s |
| | 2" | 2.44 | t (7) | 34.5 | t |
| | 3" | 1.60 | quint (7) | 26.0 | t |
| | 4" | 1.31 obsc. | | 30.6 | t |
| | 5"–12" | 1.27 | s | 30.9 to 30.3 | t |
| | 13" | 1.50 | m (7) | 29.0 | d |
| | 14" | 1.15 | q (7) | 40.1 | t |
| | 15" | 0.86 | d (6) | 23.0 | q |
| | 16" | 0.86 | d (6) | 23.0 | q |

Consistent with this, the acid hydrolysis of lipoglycopeptide 1 followed by derivatization with phenylisothiocyanate and HPLC analysis reveals the presence of glycine and alanine in the ratio 1:2. The other prominent features in the NMR spectra of lipoglycopeptide 1 include resonances for a 6-deoxy sugar and a long acyl chain. The long acyl chain is 16 carbons in length, in accordance with the proposed molecular formula and MS fragmentation (See FIG. 1 and Table 2).

TABLE 2

Diagnostic ESI MS fragments of lipoglycopeptide 1.

| Compound | M + H | a | b | c | d | e | f | g | h |
|---|---|---|---|---|---|---|---|---|---|
| 1 | m/z 1043 ($C_{46}H_{69}N_6O_{12}$) | m/z 897 ($C_{46}H_{69}N_6O_{12}$) | m/z 558 ($C_{26}H_{32}N_5O_9$) | m/z 430 ($C_{21}H_{24}N_3O_7$) | m/z 340 ($C_{20}H_{38}NO_3$) | m/z 499 ($C_{26}H_{51}N_4O_5$) | m/z 704 ($C_{32}H_{42}N_5O_{13}$) | m/z 633 ($C_{29}H_{37}N_4O_{12}$) | m/z 576 ($C_{27}H_{34}N_3O_{11}$) |

Figure 2:
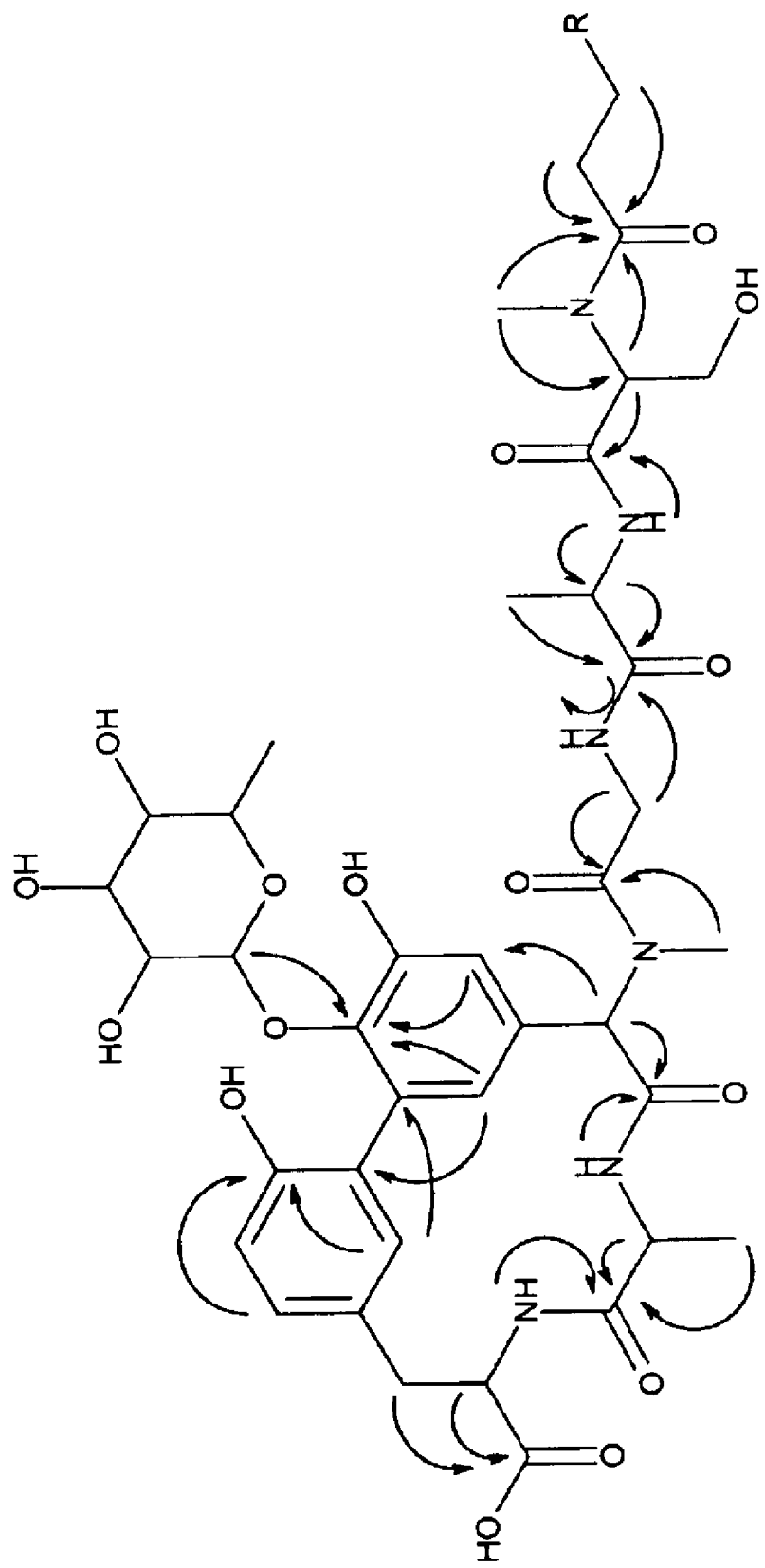
FIG. 2 shows the selected $^1$H to $^{13}$C HMBC correlations of lipoglycopeptide 1.

Further, the NMR spectrum suggests that the acyl chain terminates with an isopropyl group in lipoglycopeptide 1 ($\delta_H$ 0.86, d, J=6 Hz, 6 protons) and with a normal methyl group in lipoglycopeptide 2 ($\delta_H$ 0.89, t, J=7 Hz, 3 protons). The HMBC (hetero nuclear multiple bond correlation) correlation (FIG. 2) observed from the carbonyl carbon (amide carbonyl of N-methyl-serine δ 176.9) to the $CH_2$ protons (δ 2.44) of the acyl chain, N—$CH_3$ protons (δ 3.09) of N-methylserine and α proton (δ 4.97) of the N-methylserine strongly suggests attachment of the long acyl chain on the N-terminus of N-methylserine. Likewise, the HMBC correlations observed from the sugar anomeric proton (δ 5.36) and the mutually coupled phenylglycine protons (δ 6.47 and 6.77) to the same carbon (C-4 of N-methyl-phenylglycine δ 143.8) clearly indicate that the 6-deoxy sugar unit is attached to the 4 position of the phenylglycine through a glycosidic linkage (anomeric carbon resonance at δ 103.9). The HMBC data ($^{13}C$—$^1H$ correlations between the carbonyl and the adjacent amino acid amide proton and or proton attached to the α carbon) establishes the linear amino acid sequence as (N-methyl-serine)-alanine-glycine-(3,4,5-trisubstituted N-methyl-phenylglycine)-alanine-(3-substituted tyrosine) and is confirmed by ROESY (correlations from the amide proton to the adjacent amino acid α-proton) data (Table 3).

TABLE 3

ROESY data of lipoglycopeptide 1

| NOE From | | | | NOE To | | |
|---|---|---|---|---|---|---|
| AA | Proton | δ | Intensity | AA | Proton | δ |
| NMeSer | N—$CH_3$ | 3.09 | m | Ala 1 | NH | 8.33 |
| | | | m | NMeSer | A | 4.97 |
| | | | m | NMeSer | β-1 | 4.02 |
| | | | m | NMeSer | β-2 | 3.91 |
| | | | s | Side chain | 2' | 2.44 |
| | α | 4.97 | m | Ala 1 | NH | 8.33 |
| | | | m | NMeSer | β-1 | 4.02 |
| | | | m | NMeSer | β-2 | 3.91 |
| | | | w | NMeSer | N—$CH_3$ | 3.09 |
| | β-1 | 4.02 | m | NMeSer | α | 4.97 |
| | | | w | NMeSer | N—$CH_3$ | 3.09 |
| | β-2 | 3.91 | m | NMeSer | α | 4.97 |
| | | | m | NMeSer | N—$CH_3$ | 3.09 |
| Ala-1 | NH | 8.33 | s | NMeSer | α | 4.97 |
| | | | m | Ala 1 | α | 4.47 |
| | | | m | Ala 1 | β | 1.38 |
| | α | 4.47 | s | Ala 1 | NH | 8.33 |
| | | | s | Ala 1 | β | 1.38 |
| | β | 1.38 | m | Ala 1 | NH | 8.33 |
| | | | s | Ala 1 | α | 4.47 |
| Gly | NH | 8.30 | m | Ala 1 | α | 4.47 |
| | | | w | Gly | α-1 | 4.22 |
| | | | w | Gly | α-2 | 4.07 |
| | α-1 | 4.22 | s | Gly | α-2 | 4.07 |
| | | | s | Phegly | N—$CH_3$ | 2.82 |
| | α-2 | 4.07 | s | Gly | α-1 | 4.22 |
| | | | m | Phegly | N—$CH_3$ | 2.82 |
| Phegly | N—$CH_3$ | 2.82 | w | Phegly | 2 | 6.77 |
| | | | w | Phegly | 6 | 6.47 |
| | | | w | Phegly | α | 6.25 |
| | | | s | Gly | α-1 | 4.22 |
| | | | s | Gly | α-2 | 4.07 |
| | α | 6.25 | s | Ala 2 | NH | 8.54 |
| | | | s | Phegly | 2 | 6.77 |
| | 2 | 6.77 | s | Phegly | α | 6.25 |
| | | | m | Phegly | N—$CH_3$ | 2.82 |
| | 6 | 6.47 | m | Ala 2 | NH | 8.54 |
| | | | w | Tyr | NH | 8.35 |
| | | | s | Tyr | 2 | 6.86 |
| | | | m | Ala 2 | α | 4.79 |
| | | | m | Phegly | N—$CH_3$ | 2.82 |
| Ala 2 | NH | 8.54 | m | Phegly | 6 | 6.47 |
| | | | s | Phegly | α | 6.25 |
| | | | w | Ala 2 | α | 4.79 |
| | α | 4.79 | w | Ala 2 | NH | 8.54 |
| | | | s | Tyr | NH | 8.35 |
| | | | s | Ala 2 | β | 1.31 |
| | β | 1.31 | m | Ala 2 | NH | 8.54 |
| | | | s | Ala 2 | α | 4.79 |
| Tyr | NH | 8.35 | w | Tyr | 2 | 6.86 |
| | | | s | Ala 2 | α | 4.79 |
| | | | w | Tyr | β-2 | 3.07 |
| | α | 4.55 | w | Tyr | NH | 8.35 |
| | | | s | Tyr | 2 | 6.86 |
| | | | m | Tyr | β-1 | 3.37 |
| | | | w | Tyr | β-2 | 3.07 |
| | β-1 | 3.37 | w | Tyr | 6 | 7.03 |
| | | | w | Tyr | 2 | 6.86 |
| | | | m | Tyr | α | 4.55 |
| | | | s | Tyr | β-2 | 3.07 |
| | β-2 | 3.07 | w | Tyr | 6 | 7.03 |
| | | | s | Tyr | β-1 | 3.37 |
| | 2 | 6.86 | w | Ala 2 | NH | 8.54 |
| | | | m | Tyr | NH | 8.35 |
| | | | s | Phegly | 6 | 6.47 |
| | | | s | Tyr | α | 4.55 |
| | | | m | Tyr | β-1 | 3.37 |
| | 5 | 6.78 | m | Tyr | β-1 | 3.37 |
| | | | s | Tyr | 6 | 7.03 |
| | 6 | 7.03 | s | Tyr | 5 | 6.78 |
| | | | w | Tyr | β-1 | 3.37 |
| | | | m | Tyr | β-2 | 3.07 |
| Side chain | 2' | 2.44 | s | NMeSer | N—CH3 | 3.09 |
| | | | s | Side chain | 4' | 1.32 | w weak
m medium
s strong

The molecular formula of lipoglycopeptide 1, $C_{52}H_{78}N_6O_{16}$, requires seventeen degrees of unsaturation. The six amino acid carbonyls, one acyl group, one sugar unit, and two aromatic rings account for sixteen of the seventeen degrees of unsaturation. This suggests that the peptide is monocyclic. The HMBC correlations observed from H-2 of tyrosine to C-5 of N-methyl-phenylglycine and H-6 of N-methyl-phenylglycine to C-3 of tyrosine indicate that the two aromatic amino acids are linked via a carbon-carbon bond resulting in the 14-membered cyclic structure as shown in formula I. This is further confirined by a strong ROESY correlation observed between the H-2 of tyrosine and H-6 of N-methyl-phenylglycine (See Table 3 above).

The significant fragments observed in the Q-TOF mass spectrometry (FIG. 1 and Table 2) corroborate the structure assignment of lipoglycopeptide 1 by NMR spectroscopy.

In regard to stereochemistry, acid hydrolysis of lipoglycopeptide 1 followed by HPLC analysis of the amino acid hydrolyzate after derivatization reveals L configuration for one alanine and D configuration for the other alanine (Aswad, D. W. (1984) Analytical Biochemistiy, 137, 405–409). The coupling constant analysis of the sugar protons (Table 1) and ROESY data establish the identity of the deoxy sugar 9 as deoxy-α-mannose. Thus, small coupling constants observed between H-1 and H-2, and H-2 and H-3 are consistent with equatorial/axial (H-1), equatorial (H-2), and axial (H-3) orientations for all these protons. The large coupling constants observed between H-3 and H-4, and H-4 and H-5 are consistent with axial orientations for all these protons. Accordingly, in the ROESY experiment, a strong correlation is observed between the 1,3-diaxially oriented H-3 and H-5, and no correlation is observed between H-1 (equatorial) and H-3 (axial). The absence of ROESY correlation between H-3 and H-1 clearly demonstrates equatorial orientation for the H-1.

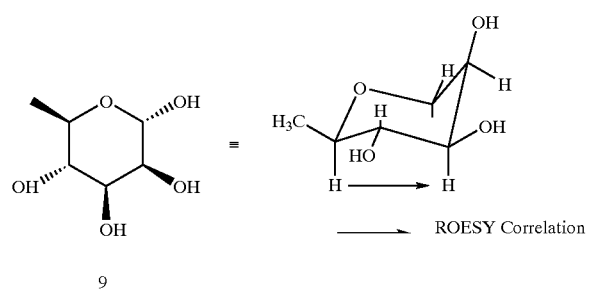

9

→ ROESY Correlation

The related lipoglycopeptide 5 has the molecular formula $C_{52}H_{78}N_6O_{15}$ as deduced by the high resolution ESIMS data (Calculated for $C_{52}H_{79}N_6O_{15}$ 1027.5603 (M+H), observed 1027.5637), which differ from lipoglycopeptide 1 by one less oxygen. The $^1H$ NMR spectrum of 5 overall contains resonances reminiscent of a lipoglycopeptide and is very similar to lipoglycopeptide 1 except that the aromatic ring of the N-methyl-phenylglycine residue is tri-substituted instead of being tetra-substituted (Table 4), indicating the lipoglycopeptide 5 is a dehydroxy analog of lipoglycopeptide 1.

TABLE 4

$^1H$ and $^{13}C$ NMR Chemical Shift Assignments of lipoglycopeptide 5 in $CD_3OD$

| AA | Position | 1H δ | m (J Hz) | 13C δ |
|---|---|---|---|---|
| NMeSer | N—CH3 | 3.10 | s | 33.4 |
| | α | 4.95 | dd (7.5, 6) | 60.7 |
| | β1 | 4.02 | dd (12, 6) | 60.4 |
| | β2 | 3.91 | dd (12, 7.5) | |
| Ala 1 | α | 4.48 | q (7) | 50.0 |
| | β | 1.40 | d (7) | 17.7 |
| Gly | α1 | 4.25 | d (17) | 42.2 |
| | α2 | 4.03 | d (17) | |

TABLE 4-continued $^1H$ and $^{13}C$ NMR Chemical Shift Assignments of lipoglycopeptide 5 in $CD_3OD$

| AA | Position | 1H δ | m (J Hz) | 13C δ |
|---|---|---|---|---|
| PheGly | N—CH3 | 2.81 | s | 32.4 |
| | α | 6.33 | s | 61.5 |
| | 1 | — | | — |
| | 2 | 7.21 | dd (8, 2) | 130.4 |
| | 3 | 7.31 | d (8) | 116.6 |
| | 4 | — | | — |
| | 5 | — | | — |
| | 6 | 6.99 | d (2) | 136.3 |
| Ala 2 | α | 4.81 | q (7) | 50.3 |
| | β | 1.32 | d (7) | 19.0 |
| Tyr | α | 4.57 | m | 55.6 |
| | β1 | 3.38 (obsc.) | | 35.4 |
| | β2 | 3.07 | dd (16, 9) | |
| | 1 | — | | — |
| | 2 | 6.78 | d | 134.2 |
| | 3 | — | | — |
| | 4 | — | | — |
| | 5 | 6.74 | d (8) | 116.7 |
| | 6 | 7.03 | dd (8, 2) | 130.5 |
| Sugar | 1' | 5.56 | d | 100.3 |
| | 2' | 4.13 | dd (2, 3) | 71.9 |
| | 3' | 3.63 | dd (9, 3.5) | 71.9 |
| | 4' | 3.36 | t (9) | 73.5 |
| | 5' | 3.39 (obsc.) | | 70.5 |
| | 6' | 1.12 | d (6) | 17.7 |
| Side chain | 2" | 2.44 | t (7) | 34.3 |
| | 3" | 1.62 | quint. (7) | 25.9 |
| | 4" | 1.33 obsc. | | 30.2 |
| | 5"–12" | 1.28 | s | — |
| | 13" | 1.51 | nonat (7) | 28.9 |
| | 14" | 1.16 | q(7) | 40.0 |
| | 15" | 0.87 | d(7) | 22.8 |
| | 16" | 0.87 | d(7) | 22.8 |

*Assigned from the HSQC experiment

It is noteworthy to mention that the lack of the phenolic group ortho to the sugar substituent results in the restoration of the sugar methyl to the normal frequency ($\delta_H$ 0.64 ppm in lipoglycopeptide 1 vs 1.12 ppm in lipoglycopeptide 5).

The structures of the remaining lipoglycopeptides 3, 4 and 6–8 are suggested by the high resolution ESIMS data (Table 5) and confinued by $^1H$ NMR data (not shown).

TABLE 5

High Resolution ESIMS data of lipoglycopeptides 1–8.

| Compound | Molecular Formula | Calculated Mass [M + H] | Observed Mass [M + H] |
|---|---|---|---|
| 1 | $C_{52}H_{78}N_6O_{16}$ | 1043.5553 | 1043.5531 |
| 2 | $C_{52}H_{78}N_6O_{16}$ | 1043.5553 | 1043.5551 |
| 3 | $C_{51}H_{76}N_6O_{15}$ | 1013.5447 | 1013.5500 |
| 4 | $C_{51}H_{76}N_6O_{15}$ | 1013.5447 | 1013.5485 |
| 5 | $C_{52}H_{78}N_6O_{15}$ | 1027.5603 | 1027.5637 |
| 6 | $C_{50}H_{74}N_6O_{15}$ | 999.5291 | 999.5318 |
| 7 | $C_{50}H_{74}N_6O_{15}$ | 999.5291 | 999.5316 |
| 8 | $C_{50}H_{74}N_6O_{16}$ | 1015.5175 | 1015.5239 |

The family of lipoglycopeptides obtained from the Streptonlyces sp. can, in general, be classified into two major cores differing only in the oxidation state of the N-methyl-phenylglycine residue. The rest of the diversity stems from the nature of the acyl chain that differ in chain length and degree of branching.

EXAMPLE 5

Deacylation of Lipoglycopeptides 7 and 8

A mixture containing primarily lipoglycopeptides 7 and 8 (200 mg) is dissolved in 20 ml of acetonitrile-water-trifluroacetic acid (6:3:1) and the solution is stirred for 90 hr. at room temperature. After this time, the reaction mixture is concentrated in vacuo to dryness, dissolved in 5 ml of methanol and purified over a Poly LC polyhydroxyethyl aspartamide column (PolyLC Inc., Cat. # BMHY120 50.8× 250 mm, 12 micron, flow rate 45 ml/min, 90–50% acetonitrile gradient buffered with 0.05% ammonium acetate over 72 min) to yield two fractions. The two fractions are further purified independently over a CG161 column (85 ml) to yield 10.7 mg of glycopeptide and 14 mg of glycopeptide 11. Approximately 28% of unreacted starting materials are also recovered from the reaction misture.

High resolution ESI mass spectrometry suggests the molecular formula $C_{36}H_{48}N_6O_{14}$ (Calculated for $C_{36}H_{49}N_6O_{14}$, 789.3307 (M+H), observed 789.3324) and $C_{36}H_{48}N_6O_{15}$ (Calculated for $C_{36}H_{49}N_6O_{15}$, 805.3256 (M+H), observed 805.3272) for the deacylated glycopeptides 10 and 11, respectively. The structures of glycopeptides and 11 as depicted in the formula, below are further supported by the $^1$H NMR data (Table 6).

TABLE 6

$^1$H and $^{13}$C NMR Chemical Assignments of glycopeptides 10 and 11 in $CD_3OD$

| AA | Position | 10 $^1$H δ | 10 m(J Hz) | 11 $^1$H δ | 11 m(J Hz) |
|---|---|---|---|---|---|
| NMeSer | N—CH3 | 2.37 | s | 2.37 | s |
|  | α | — | — | — | — |
|  | β1 | 3.72 | dd (11, 5.5) | 3.73 | dd (11, 5.5) |
|  | β2 | 3.65 | dd (11, 6.5) | 3.65 | dd (11, 7) |
| Ala | α | 4.53 | q (7) | 4.53 | q (7) |
|  | β | 1.43 | d (7) | 1.43 | d (7) |
| Gly | α1 | 4.27 | d (17) | 4.30 | d (17) |
|  | α2 | 4.01 | d (17) | 3.98 | d (17) |
| PheGly | N—CH3 | 2.81 | s | 2.84 | s |
|  | α | 6.32 | s | 6.26 | s |
|  | 1 | — | — | — | — |
|  | 2 | 7.21 | dd (8.5, 2.5) | 6.73 | brs |
|  | 3 | 7.29 | d (8.5) | — | — |
|  | 4 | — | — | — | — |
|  | 5 | — | — | — | — |
|  | 6 | 7.01 | d (2) | 6.53 | brs |
| Ala | α | 4.80 | q (7) | 4.78 | q (7) |
|  | β | 1.32 | d (7) | 1.32 | d (7) |
| Tyr | α | 4.50 | dd (8, 4) | 4.53 (obsc.) | — |
|  | β1 | 3.38 (obsc.) | — | 3.42 | dd (15.5,) |
|  | β2 | 3.07 | dd (15.5, 8) | 3.10 | dd (15.5, 7.5) |
|  | 1 | — | — | — | — |
|  | 2 | 6.79 | d (2) | 6.89 | brs |
|  | 3 | — | — | — | — |
|  | 4 | — | — | — | — |
|  | 5 | 6.73 | d (8) | 6.76 | d (8) |
|  | 6 | 7.02 | dd (8, 2) | 7.05 | d (8) |
| Sugar | 1' | 5.56 | d (1.5) | 5.39 | brs |
|  | 2' | 4.13 | dd (3, 2) | 4.23 | brm |
|  | 3' | 3.62 | — | 3.73 | — |
|  | 4' | 3.35 (obsc.) | t (9) | 3.26 (obsc.) | t (9.5) |
|  | 5' | 3.19 | dq (9, 7) | 3.19 | dq (9, 6) |
|  | 6' | 1.12 | d (7) | 0.67 | d (6) |

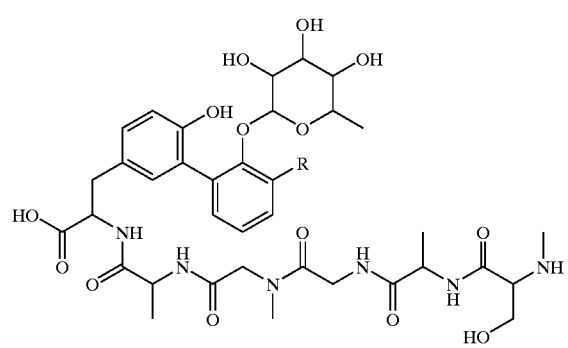

10 R = H

11 R = OH

A significant upfield shift (~0.7 ppm) experienced by the N-methyl resonance of N-methyl-serine residue in glycopeptides 10 and 11 when compared to lipoglyclopeptides 1 and 5 clearly substantiates the attachment of the acyl chain to the N-terminus of the N-methyl-serine.

The deacylation procedure described herein can also be used to deacylate compounds 1–6.

EXAMPLE 6

Purification of E. coli and S. pneumoniae SPases

Cloning and expression of the E. coli SPase I gene is performed by polymerase chain reaction (PCR) using E. coli genomic DNA as a template and two oligonucleotides as primers: 5'-CGATCGTTCATATGGTTCGTTCATTTCTTTATGAA-CCCTTTCAG-3' (SEQ ID NO: 1) and 5'-GCCGCTAACTCGAGGGCAGCGTGAACGATCA-TTTCATCACAG-3' (SEQ ID NO:2). The primers are designed to contain NdeI and XhoI restriction sites at the 5'-ends, respectively, to enable cloning into the bacterial expression vector pET15b (Novagen). The primers are synthesized based upon the published sequence of E. coli SPase I (Wolfe, et al. (1983) *J. Biol. Chem.* 258, 12073–12080).

Expression vector pET15b-E. coli SPase is constructed by replacing the NdeI/XhoI fragment of pET15b with the PCR fragment that is purified and digested with NdeI and XhoI. The identity of the cloned gene is confirmed by DNA sequencing. For expression of E. coli SPase I, E. coli strain BL21(DE3)(Stratagene) is transformed with pET15b-E. coli SPase, and grown and induced with 0.4 mM IPTG (isopropryl-1-thio-β-D-galactopyranoside) as described in Studier, et al. (1990) *Methods Enzymol.* 185, 60–89.

For purification of E. coli SPase T, one liter of IPTG-induced E. coli BL21(DE3) cells harboring pET15b-E coli SPase is harvested by centrifugation and re-suspended in 50 ml of lysis buffer containing 50 mM $Na_2HPO_4$, 300 mM NaCl, pH 8.0, and sonicated 5 min. on ice. The lysate is then centrifuged at 50,000 g for 1 hr at 4° C. The resultant supernatant is discarded, the pellet is re-suspended, and sonicated for 5 min. in 20 ml of lysis buffer containing 8 M urea. After centrifugation at 50,000 g for 1 hr at 4° C., the supernatant is loaded onto a 5 ml column of pre-equilibrated Ni-nitrilotriacetic acid (NTA) that is then washed with 120 ml of refolding buffer (50 mM $NaH_2PO4$, 300 mM NaCl, 15 mM imidazole) containing a continuous urea gradient from 6 to 1 M with a flow rate of 1 ml/min. The protein is eluted with 20 ml of elution buffer (20 mM Tris-HCl, pH 8.0, 20% glycerol, 1 M urea and 100 mM imidazole), and 1 ml fractions are collected and utilized for enzyme assay.

Procedures for cloning, expression and purification of S. pneumoniae Spase can be found in reference (Peng, et al. (2001) J. Bacterol. 183, 621–627).

EXAMPLE 7

$IC_{50}$ Determinations

"$IC_{50}$" refers to the concentration of inhibitor required to achieve a half-maximal degree of inhibition of SPase I. The $IC_{50}$ is determined by a fluorimetric assay as described in Peng, et al. (2001) J. Bacterol. 183, 621–627, with a fluorogenic peptide used as substrate as described therein. The reaction is performed in 50 μls of reaction mixture containing 50 nM of either E. coli or S. pneumoniae SPase I, 50 μM substrate, and a series dilution of inhibitor. Inhibitors are dissolved in dimethylsulfoxide (DMSO). Compounds in DMSO are diluted in reaction buffer. The final DMSO concentration in the reaction mixtures is 2% (v/v). Reaction mixtures are incubated at 37° C. for 1–2 hrs. The $IC_{50}$ is calculated using a nonlinear regression method with GraphPad Prism™ Software (GraphPad G3-A13127-507). The inhibitory activity of lipoglycopeptides 1–8 against both E. coli and S. pneumoniae signal peptidases, are summarized in Table 7. As shown in Table 7, all eight compounds exhibit potent activity against both E. coli ($IC_{50}$ ranging from 0.11 to 0.19 μM) and S. pneumoniae ($IC_{50}$ ranging from 2.4–10.2 μM) signal peptidases with greater inhibitory activity apparent toward the E. coli signal peptidase.

TABLE 7

Inhibition of E. coli and S. pneumoniae signal peptidases by lipoglycopeptides 1– 8.

| Compound | $IC_{50}$ (μM) | |
| --- | --- | --- |
|  | E. coli | S. pneumoniae |
| 1 | 0.17 | 7.1 |
| 2 | 0.19 | 10.3 |
| 3 | 0.13 | 7.0 |
| 4 | 0.13 | 5.9 |
| 5 | 0.13 | 2.4 |
| 6 | 0.11 | 6.6 |
| 7 | 0.11 | 6.1 |
| 8 | 0.11 | 24.9 |

EXAMPLE 8

Kinetic Analysis

A kinetic analysis is performed with E. coli SPase I and the non-fluorogenic peptide substrate by HPLC assay as described in Peng, et al. (2001) J. Bacterol. 183, 621–627. 50 μl of reaction volume contains 50 nM E. coli SPase I with different concentrations of substrate and lipoglycopepetide inhibitors. The reaction mixtures are incubated at room temperature for 30 mins., and terminated by the addition of an equal amount of 8 M urea. The final concentration of DMSO in the reaction mixtures is 2%. Substrate cleavage is analyzed by HPLC as described in Peng, et al. (2001) J. Bacterol. 183, 621–627. The initial rate, $K_1$, and inhibition type of the inhibitor is calculated with Sigma Plot 2000, Version 6.2 with enzyme kinetics module (SPSS, Inc., Cat No. 3703564). The kinetic analysis indicates that these compounds are competitive inhibitors with respect to the non-fluorogenic peptide substrate, with inhibitor constants (Ki) ranging from 50–158 nM (Table 8).

TABLE 8

Inhibitor constants (Ki) of lipoglycopeptides 2, 5, 7 and 8 against E. coli signal peptidase I

| Compound | 2 | 5 | 7 | 8 |
| --- | --- | --- | --- | --- |
| Ki (nM) | 158.0 | 57.5 | 50.4 | 109.9 |

Figure 3:
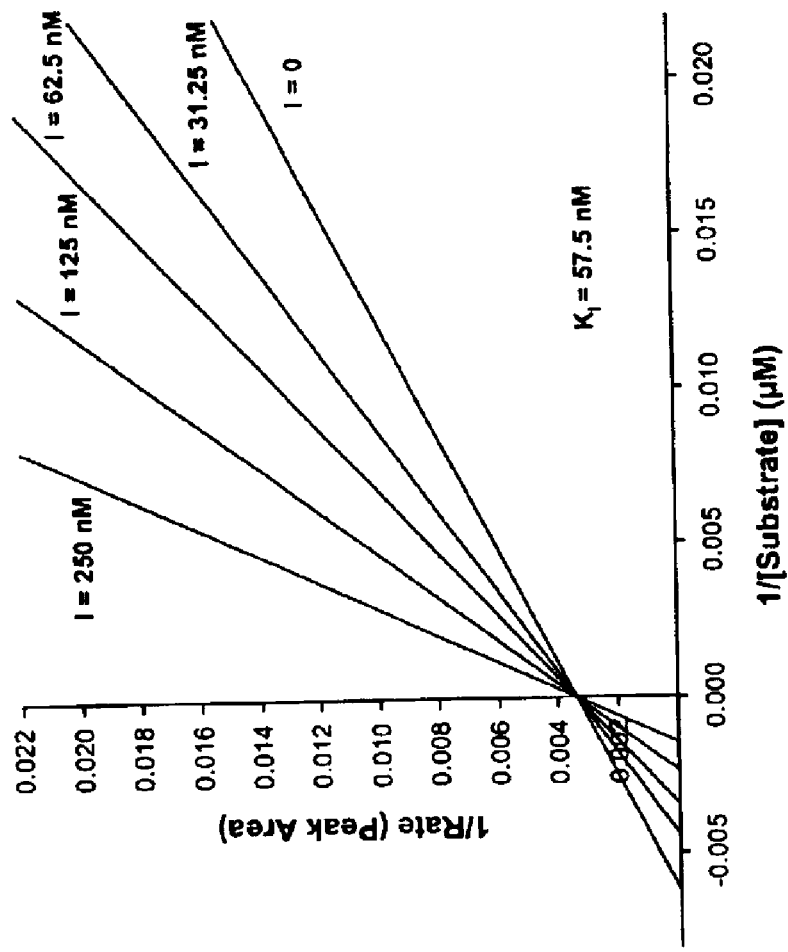
FIG. 3 shows the Lineweaver-Burk plot for the inhibition of *E. coli* signal peptidase I by lipoglycopeptide 1.

The Lineweaver-Burk plot for the inhibition of the E. coli signal peptidase I with compound 5 is shown in FIG. 3.

EXAMPLE 9

Determination of in vitro Antibacterial Activity of Lipoplycopeptides

The in vitro antibacterial activity of lipoglycopeptides 1, 2, 5, 6, 7, and 8 is determined according to the National Committee for Clinical Laboratory Standards (NCCLS) recommendations for broth micro-dilution assay using 2xsTH (Todd Hewitt broth), MHII (cation adjusted Mueller Hinton broth) or HTM medium (Haemophilus Test Medium) (Gerhardt, P., et al., (1994) Methods for General and Molecular Bacteriology. American Society for Microbiology, Washington, D.C.). Bacterial strains used for antibacterial assay include both gram-positive and gram-negative bacteria: S. pneumoniae R6, Staphylococcus aureus SA027, Haemophilus influenzae ATCC 49247, E. coli EL683 and EL744. A two-fold serial dilution of the test compound is prepared in 100% DMSO. The assay is performed in the wells of a sterile 96-well microplate, that is inoculated with bacterial cell suspension in growth medium or broth as above. The final volume is 100 μl cell suspension, containing 2.5% DMSO. The starting concentration of bacterial cells is $5 \times 10^5$ CFU/ml. The 96-well microplate is incubated for 23–24 hr at 37° C. in an ambient air incubator. Upon completion of incubation, the MIC (minimal inhibitory concentration) is determined by visual examination of the microplate with the aid of a magnifying mirror apparatus. The MIC is the lowest concentration of compound tested that results in no visible sign of bacterial growth. As shown in Table 9, lipoglycopeptides 1, 2, 5, 6, 7, and 8 demonstrate antibacterial activity, against both gram negative and gram positive bacteria, for example MICs of 4–32 μg/ml against E. coli, 8->64 μl against S. pneumoniae, 32->64 μg/ml against S. aureus, and 64->64 μg/ml against H. influenzae.

TABLE 9

In vitro antibacterial activity of lipoglycopeptides 1, 2, 5, 6–8

| | MIC (µg/ml) | | | | |
|---|---|---|---|---|---|
| Compound | S. pneumoniae, R6 2XsTH broth | S. aureus, SA027 MHII broth | H. influenzae ATCC49247 HTM broth | E. coli, EL683 MHII broth | E. coli, EL744 MHII broth |
| 1 | 16 | 32 | 64 | 8 | 32 |
| 2 | 8,16 | 64 | 64 | 8 | 32 |
| 5 | 16, 8 | >64 | >64 | 4 | 16 |
| 6 | 64 | >64 | >64 | — | 8 |
| 7 | >64 | >64 | >64 | — | 16 |
| 8 | >64 | >64 | >64 | — | 8 |

EXAMPLE 10

Beta-lactamase Release Assay

In *Staphylococcus aureus*, signal peptidase cleaves beta-lactamase, resulting in the release of beta-lactaidase into the medium. In this example, the ability of lipoglycopeptides 1,2, and 5 to inhibit the release of beta-lactamase from *Staphylococcus aureus* into the medium is examined.

*Staphylococcus aureus* (ATCC 33592) cells are grown overnight in a series dilution in Brain Heart Infusion (BHI) (Gerhardt, P., et al., (1994) *Methods for General and Molecular Bacteriology*. American Society for Microbiology, Washington, D.C.) medium in a 37° C. incubator containing 5% $CO_2$. Cultures with an $OD_{660}$ less than 0.3 are centrifuged, and the cells are washed once with fresh BHI medium. The cells are then resuspended in fresh BHI medium to an initial $OD_{660}$ of 0.15–0.2. At the same time, the selected inhibitor is diluted from the DMSO stock solution into BHI medium at different concentrations, and is added to the cells which are then incubated at 37° C. under 5% $CO_2$ for 2 hr. The final DMSO concentration in the reaction mixtures is 1% (v/v). The $OD_{660}$ is measured at the end of incubation. The cells are centrifuged, and the supernatant is saved for the determination of secreted beta-lactamase. The pellet is washed once with fresh BHI medium, re-suspended in the equivalent volume of fresh BHI medium, frozen, and then thawed at −80° C. for three cycles, and used for the determination of retained beta-lactamase. For the determination of beta-lactamase activity, 100 µl reaction mixture (30–50 µls of supernatant or lysed cells) is incubated with 250 µM nitrocefin in 1×PBS buffer (phosphate buffered saline) (pH 6.8) at 37° C. for 30–60 min. Nitrocefin is the substrate for beta-lactamase. Cleavage of nitrocefin results in an increase in absorbance at 482 nm. The absorbance at 482 nm ($OD_{482}$) is measured at the beginning and at the end of the reaction. The secreted and the retained beta-lactamase activities are calculated based upon the $\Delta OD_{482}$.

Figure 4:
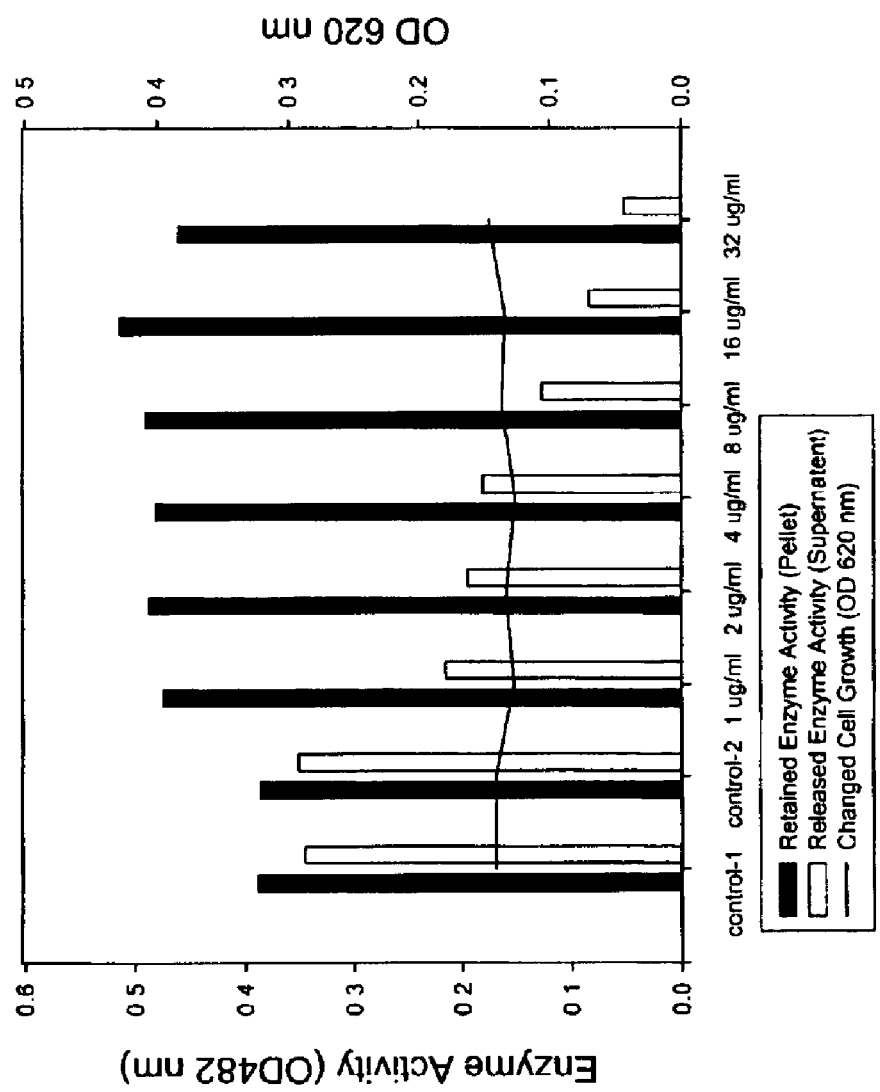
FIG. 4 shows the effect of lipoglycopeptide 5 on β-lactamase release from *Staphylococcus aureus*.

Lipoglycopeptides 1, 2 and 5 inhibit the secretion of beta-lactamase in a beta-lactamase-producing *S. aureus* strain (ATCC 33592) in a dose-dependent manner. An example of beta-lactamase secretion inhibition at different concentrations of is depicted in FIG. 4. This result strongly suggests that the antibacterial activity observed with the present lipoglycopeptides is due to the inhibition of signal peptidase I within the cells. Cleavage of secreted proteins in bacterial cells is essential for cell growth: inhibition of signal peptidase I interferes with protein secretion in bacterial cells, which is required for the normal growth and development of bacterial cells (Dalbey, et al. (1997) *Protein Sci.* 6, 1129–1138).

The invention being thus described, it is obvious that the same can be varied in many ways. Such variations are not to be regarded as a departure from the spirit and scope of the present invention, and all such modifications as would be obvious to one skilled in the art are intended to be included within the scope of the following claims.

---

What is claimed is:

1. An isolated compound comprising the structure shown in formula I:

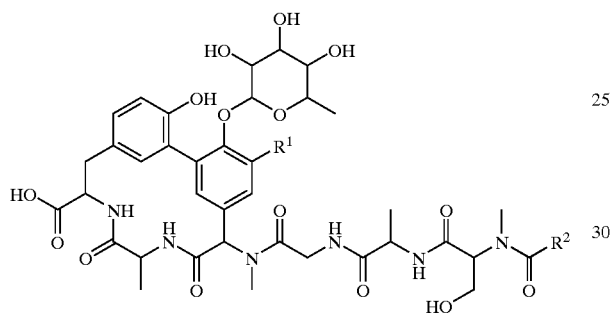

(I)

wherein $R^1$ is H or OH, and $R^2$ is a $C_{14}$–$C_{16}$ alkyl group, or a pharmaceutically acceptable salt thereof.

2. A composition, comprising said compound of claim 1, and a buffer, carrier, diluent, or excipient.

3. A pharmaceutical composition, comprising said compound of claim 1, and a pharmaceutically acceptable buffer, carrier, diluent, or excipient.

* * * * *

SEQUENCE LISTING

<160> NUMBER OF SEQ ID NOS: 2

<210> SEQ ID NO 1
<211> LENGTH: 44
<212> TYPE: DNA
<213> ORGANISM: Escherichia coli
<300> PUBLICATION INFORMATION:
<301> AUTHORS: Wolfe et al.
<303> JOURNAL: Journal of Biological Chemistry
<304> VOLUME: 258
<306> PAGES: 12073-12080
<307> DATE: 1983

<400> SEQUENCE: 1
cgatcgttca tatggttcgt tcatttcttt atgaaccctt tcag            44

<210> SEQ ID NO 2

```
<211> LENGTH: 42
<212> TYPE: DNA
<213> ORGANISM: Escherichia coli
<300> PUBLICATION INFORMATION:
<301> AUTHORS: Wolfe et al.
<303> JOURNAL: Journal of Biological Chemistry
<304> VOLUME: 258
<306> PAGES: 12073-12080
<307> DATE: 1983

<400> SEQUENCE: 2
gccgctaact cgagggcagc gtgaacgatc atttcatcac ag                42
```